United States Patent [19]

Parodos et al.

[11] Patent Number: 5,084,565

[45] Date of Patent: Jan. 28, 1992

[54] **PROBES FOR THE SPECIFIC DETECTION OF *ESCHERICHIA COLI* AND SHIGELLA**

[75] Inventors: Kyriaki Parodos, Framingham; Hsien-Yeh Hsu, Brighton; David Sobell, Arlington; Janice M. McCarty, Hyde Park; David J. Lane, Milford, all of Mass.

[73] Assignee: Gene-Trak Systems, Framingham, Mass.

[21] Appl. No.: 233,683

[22] Filed: Aug. 18, 1988

[51] Int. Cl.$^5$ .................... C07H 21/00; C12Q 1/68
[52] U.S. Cl. ............................ 536/27; 435/6; 435/91; 435/839; 435/843; 435/844; 435/849; 435/852; 435/856; 435/875; 435/879; 435/880; 435/882; 435/883; 435/884; 435/885; 435/886; 436/501; 436/808; 536/26; 536/28; 935/9; 935/78

[58] Field of Search ............ 435/6, 91, 839, 843, 435/844, 849, 852, 856, 875, 879, 880, 882, 883, 884, 885, 886; 436/501, 808; 536/27, 26, 28; 935/9, 78

[56] References Cited

U.S. PATENT DOCUMENTS 4,816,389  3/1989  Sansonetti et al. .................... 435/6

Primary Examiner—Robert A. Wax
Assistant Examiner—Ardin H. Marschel
Attorney, Agent, or Firm—Norval B. Galloway; William H. Magidson; Ralph C. Medhurst

[57] ABSTRACT

Nucleic acid probes capable of specifically hybridizing to rRNA of *E. coli* and Shigella species and not to rRNA of non-*E. coli*/Shigella are described along with methods utilizing such probes for the specific detection of *E. coli* and/or Shigella in food and other samples.

10 Claims, No Drawings

PROBES FOR THE SPECIFIC DETECTION OF *ESCHERICHIA COLI* AND SHIGELLA

FIELD OF THE INVENTION

This invention relates to detecting bacteria belonging to the species *Escherichia coli* and species of the closely related genus, Shigella. More specifically this invention provides nucleic acid probes which are capable of hybridizing to most or all *Escherichia coli* and Shigella strains, along with methods for their use for the specific detection of these organisms in clinical samples, food and other samples.

BACKGROUND OF THE INVENTION

The term "*Escherichia coli*" as used herein, refers to bacteria classified as such in Bergey's Manual of Systematic Bacteriology (N. R. Krieg [ed.1, 1984, pp408–423, Williams & Wilkins). Detection of *Escherichia coli* (*E. coli*) is important in various medical and public health contexts. *Escherichia coli* (*E. coli*) was discovered to be ubiquitous in fecal material nearly a century ago. Thus, foods are tested for *E. coli* as the indicator organism for fecal contamination. Generally, the presence of *E. coli* in food and water is used as a measure of sanitary conditions. *E. coli* infection itself also can cause a variety of symptoms ranging from mild to severe gastroenteritis. A large variety of food and environmental samples are potential sources of human *E. coli* infection but routine screening is both time consuming and difficult.

It is, therefore, an aspect of the present invention to provide a novel assay system capable of rapidly detecting *E. coli* and which is generally applicable to environmental, food or clinical samples. The probes of the present invention also detect all Shigella species and strains tested to date (Table 2). Shigella, as used herein, refers to bacteria classified as such in Bergey's Manual of Systematic Bacteriology (ibid., pp. 423–427). Shigella is primarily a pathogen of man and other primates, and is a causative agent of bacillary dysentery. Members of the genus Shigella are extremely closely related to members of the genus Escherichia and exhibit considerable overlap in genetic, biochemical and pathogenic characteristics with members of the latter genus. Although Shigella is only rarely isolated from food samples or from fecal material of normal healthy humans, its presence in a test sample would clearly also be an indication of fecal contamination.

It is another aspect of the present invention to provide a diagnostic assay for the detection of *E. coli* plus Shigella in a test sample.

Pursuant to a standard laboratory method and a method recommended by the FDA (FDA/BAM Bacteriological Analytical Manual, Chapters 5 and 6, 6th Edition, 1984, Supplement 9/87', Association of Offical Analytical Chemists), the presence of *E. coli* has been traditionally detected by culturing an appropriately prepared sample on microbiological media under conditions favorable for growth of these organisms. The resulting colonies are then typically examined for morphological and biochemical characteristics, a process that generally is initiated 48 hours after acquisition of the sample and disadvantageously takes between four to six days to complete.

A recent, more rapid method for detection of *E. coli*, developed by Feng and Harmant (Appl. and Environ. Microbiol., 1982, 43:1320–1329), uses 4-methylumbelliferyl-$\beta$-D-glucuronide (MUG). The MUG assay is a fluorogenic test for the enzyme $\beta$-glucuronidase. According to Kilian and Bulow (Acta Path. Microbiol. Scand., Sect. B, 1976, 84:245–251), 97% of *E. coli* strains possess $\beta$-glucuronidase. The basic premise is that the rapid confirmation of *E. coli* is possible by incorporating MUG into a suitable culture broth, such as LST or EC. After inoculation of the broth with a test sample, fluorescence of 4-methylumbelliferone is produced from hydrolysis of MUG if $\beta$-glucuronidase is present, and can be determined by examining the sample under longwave ultraviolet light (366 nanometers) after 24–48 hours of incubation. In the commonly used format of this test, a positive *E. coli* sample shows: (1) gas production in a Durham tube, and (2) fluorescence of the broth upon illumination with ultraviolet light. However, as demonstrated by the results shown in Table 2, the MUG test yields ambiguous patterns of gas production and fluorescence for many *E. coli* strains. Particularly striking is the apparent lack of fluorescence (and, by inference, $\beta$-glucuronidase) in all tested strains of serotype $\alpha$ 0:157 H7 enteropathogenic *E. coli*.

It is yet another aspect of the present invention to avoid the disadvantages associated with these techniques and to employ nucleic acid probes to detect *E. coli* and Shigella.

It is yet another aspect of the present invention to provide probes which can hybridize to target regions which can be rendered accessible to the probes under normal assay conditions.

While Kohne et al. (1968) Biophysical Journal 8:1104–1118 discuss one method for preparing probes to rRNA sequences they do not provide the teaching necessary to make nor can they predict the existence of these probes for the specific detection of *E. coli* and *E. coli*/Shigella.

Pace and Campbell (1971) Journal of Bacteriology 107:543–547 discuss the homology of ribosomal ribonucleic acids from diverse bacterial species and a hybridization method for quantitating such homology levels. Similarly, Sogin, Sogin, and Woese (1972) Journal of Molecular Evolution 1:173–184 discuss the theoretical and practical aspects of using primary structural characterization of different ribosomal RNA molecules for evaluating phylogenetic relationships.

Fox, Pechman, and Woese (1977) International Journal of Systematic Bacteriology 27:44–57 discuss the comparative cataloging of 16S ribosomal RNAs as an approach to prokaryotic systematics. These references, however, fail to relieve the deficiency of Kohne's teaching with respect to *E. coli* and Shigella.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *E. coli*, are referred to as 5S, 16S, and 23S rRNAs. These names historically are related to the size of the RNA molecules, as determined by sedimentation rate. In actuality, however, they vary substantially in size between organisms. Nonetheless, 5S, 16S, and 23S rRNA are commonly used as generic names for the homologous RNA molecules in any bacteria, and this convention will be continued herein.

Hybridization is traditionally understood as the process by which, under predetermined reaction conditions, two partially or completely complementary single-stranded nucleic acids are allowed to come together in an antiparallel fashion to form a double-stranded nucleic acid with specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types of concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will largely dictate the preferred probes to be employed. Such relationships are well understood and can be readily manipulated by those skilled in the art. In general, dependent upon probe length, such persons understand stringent conditions to mean approximately 35° C.–65° C. in a salt solution of approximately 0.9 molar.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences.

A target nucleic acid is one to which a particular probe is capable of preferentially hybridizing.

Still other useful definitions are given as their first use arises in the following text. All references cited herein are fully incorporated by reference.

SUMMARY OF THE INVENTION

In accordance with the various principles and aspects of the present invention, there are provided nucleic acid probes and probe sets comprising DNA or RNA sequences which, under specific hybridization conditions, are capable of detecting in a test sample, the presence of ribosomal RNA (rRNA) or rDNA (gene for rRNA) molecules of *E. coli* and all known Shigella species but which are not capable, under the same conditions, of detecting the rRNA or DNA of any other related bacteria which may be present in the test sample. The present invention also features an assay system for the utilization of these probes, the format of which can advantageously enhance the aforementioned desirable behavior of the probes. In particular, a cultivation step which enhances the growth of *E. coli* relative to that of other bacteria is ideally included in the present assay. The cultivation conditions described herein also support the growth of all Shigella so far tested (Table 4) but are not specifically optimized for growth of Shigella. This microbiological selection, in combination with the specificity of the described probes, imparts the specificity for *E. coli* (and Shigella, as discussed) which the present invention exhibits.

The assay system of the present invention advantageously exhibits the following enhanced performance capabilities with respect to other currently available means for detection of *E. coli*:

a) increased sensitivity; i.e., the ability to detect *E. coli* in a given sample more frequently than currently available methods;

b) potentially significant reductions in assay cost due to the use of inexpensive reagents and reduced labor;

c) accurate identification of *E. coli* and Shigella even when the biochemically closely related non-pathogenic species, *Escherichia vulneris, Escherichia blattae* or *Escherichia hermanii* are present; and d) faster results because the test does not require the isolation of *E. coli* from the cultured sample prior to testing. Accordingly, in the preferred format, this invention advantageously takes only two days to provide a result.

It has been discovered that other advantages incurred by directing the probes of the present invention against rRNA include the fact that the rRNAs detected constitute a significant component of cellular mass. Although estimates of cellular ribosome content vary, actively growing *E. coli* bacteria may contain upwards of $5.0 \times 10^4$ ribosomes per cell, and therefore $5.0 \times 10^4$ copies of each of the three rRNA species (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes encoding them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to *E. coli* and Shigella rRNA target sequences which appear to be fully inclusive for all *E. coli* strains and all strains of all species of Shigella.

Thus, under appropriate assay conditions (i.e., selective precultivation), the probes of the invention could be used to detect *E. coli* or *E. coli* plus Shigella. As a practical matter, Shigella is encountered only rarely in food and environmental samples which are the initial focus of the preferred assay format described below. Thus, while the probes clearly are fully inclusive for all *E. coli* and all Shigella (see dot blot results, Table 2), the assay (in its initial intended use) can accurately be described either as an *E. coli* or an *E. coli* plus Shigella test.

Advantageously, these same rRNA target sequences are sufficiently different in most non-*E. coli*/Shigella rRNAs that, under the preferred assay conditions of the present invention, the probe(s) of the present invention hybridize to *E. coli* and Shigella rRNAs and do not hybridize to non-*E. coli* and Shigella rRNAs. These probe characteristics are defined as inclusivity and exclusivity, respectively. The discovery that probes could be generated with the extraordinary inclusivity and exclusivity characteristics of those of the present invention with respect to *E. coli* and Shigella was unpredictable and unexpected.

In the primary embodiment of the invention, an assay method for detecting *E. coli* is provided in which bacteria in the sample to be tested are preferably grown for a limited time under conditions which foster rapid and abundant growth of any *E. coli* in the sample (growth of Shigella, as discussed, is acceptable but not essential for indicating fecal contamination) and which are biased against the growth of many other bacteria. Hybridization analysis using the preferred probes of the present invention is then advantageously performed on the sample after this growth period.

BRIEF DESCRIPTION OF THE TABLES

Further understanding of the principles and aspects of the present invention may be made by reference to the tables wherein:

Table 1 Shows alignment of the nucleotide sequences of the preferred probes of the present invention with the nucleotide target sequence including the "core" region from 455 to 477 of *E. coli* 16S rRNA (using the *E. coli* position numbering convention) along with relevant portions of the 16S rRNAs from two representative Shigella strains, two "atypical" *E. coli*, *Salmonella typhimurium*, *Proteus vulgaris* and the *Yersinia enterocolitica* type strain ATCC 9610. RNA sequences are written 5' to 3', probe sequences are DNA and written 3' to 5'. Lower case "c" in certain of the probes indicates a modified cytosine residue to which a reporter group may or may not be attached depending on the assay format employed. Probe 787 is shown, along with the "core" region of variation upon which it is based, below the "parent" sequence, *E. coli* K-12 (Brosius et al., Biochemistry, 1978, 75:4801–4805). Probe 683 is a detection probe which is designed to be used with the 787 probe in dual probe formats.

Table 2 Exemplifies the inclusivity behavior of the preferred probes toward a representative sampling of *E. coli* and Shigella strains tested in a dot blot format. Inclusivity data related to the preferred liquid hybridization testing format of Example 1 (General) also is provided for the full collection of *E. coli* strains and a select, representative sampling of Shigella strains.

Table 3 Exemplifies the exclusivity behavior of the preferred probes toward a representative sampling of non-*E. coli* and Shigella strains. Exclusivity data related to the preferred liquid hybridization testing format of Example 1 (General) also is provided.

Table 4 Provides data showing detection of *E. coli* in food samples with the preferred probes in a preferred format of the present invention (Example 1, Specific).

DETAILED DESCRIPTION OF THE INVENTION AND BEST MODE

The first step taken in the development of the probes of the present invention involved identification of regions of 16S and/or 23S rRNA which could potentially serve as target sites for *E. coli*-specific nucleic acid probes. As a practical matter, it is difficult to predict, a priori, which non-*E. coli* organisms might be present in any test sample. Because of the large number of such potential non-*E. coli* bacteria, demonstrating exclusivity for any given probe sequence is not only unpredictable but also extremely difficult and laborious. A more rigorous criterion was adopted to obviate the need to know, during initial stages of research and development, what non-*E. coli* bacteria might be present in all test samples that ultimately will be screened using the probe. This entailed knowledge of the phylogenetic relationships among Escherichia and between Escherichia and other groups of bacteria. Specifically, an operating but previously unproven hypothesis was adopted that the exclusivity criterion could be satisfied by determining that if a particular target region in *E. coli* rRNA, sufficiently different from the homologous region in the rRNA of representative yet close evolutionary relatives of *E. coli*, could be identified, then a probe to such a sequence could be used to distinguish between the *E. coli* and the relatives by hybridization assay. Based on phylogenetic observations, it was then extrapolated that rRNA sequences of more distantly related organisms, even though their actual identity may not necessarily be known, should predictably be as or more different in the aforementioned target region of sequence than the aforementioned close evolutionary relative of *E. coli*. However, it cannot be predicted, a priori, whether such regions exist or, if they do, where within the rRNA such regions will be located.

As our first step in identifying regions of *E. coli* rRNA which could potentially serve as useful target sites for nucleic acid hybridization probes, nearly complete nucleotide sequences of the 16S and 23S rRNAs from two *E. coli* and three Shigella strains were determined. These, in conjunction with the 16S and 23S sequences of *E. coli* available in the literature, were arbitrarily selected as representative of the evolutionary breadth of species *E. coli* and the "supergenus" comprising Escherichia and Shigella. The nucleotide sequences of various portions of the rRNAs were determined by standard laboratory protocols either by cloning (Maniatis et al., 1982, Molecular Cloning: A Laboratory Manual, Cold Spring Harbor Laboratory, N.Y., 545pp) and sequencing (Maxam & Gilbert, 1977, Proceedings of the National Academy of Science, USA 4:560–564., Sanger et al., 1977, Proceedings of the National Academy of Science, USA 74:5463–5467) the genes which specify the rRNAs, and/or by direct sequencing of the rRNAs themselves using reverse transcriptase (Lane et al., 1985, Proceedings of the National Academy of Science, USA B2:6955–6959).

The identified nucleotide sequences were compared to one another and to other available rRNA nucleotide sequences, in particular to those of closely related bacteria such as Proteus, Salmonella, Morganella, Yersinia, Citrobacter, Klebsiella, Pasturella, etc.

The relationship between *E. coli* and Shigella species were of particular importance since members of these two genera are not usefully distinguished even by the extremely sensitive method of DNA/DNA hybridization (Brenner, D. J., 19B4, Bergey's Manual of Systematic Bacteriology, Vol. 1, pp 408, Krieg, N. R. and Holt, J. G., eds. Williams and Walkins, Baltimore). Indeed, it has been discovered based on extensive sequence analysis of the 16S and 23S rRNAs of two *E. coli* and five Shigella strains that complex patterns of localized differences between *E. coli* and Shigella species do exist. It was also discovered by hybridization experiments using various test probes targeted upon these regions, that most of the *E. coli* and Shigella "signature" sequences are statistically too noisy (i.e. are also sporadically found in other enteric genera and occasionally "cross" the *E. coli*/Shigella boundary as well) to use in any reasonably simple test format (data not shown).

However, one region of sequence was identified which appears to be conserved among all *E. coli* and Shigella and which, importantly, is different in all other bacterial sequences so far inspected by nucleotide sequence analysis or tested by hybridization. This preferred region of sequence is shown in Table 1.

Further experimental testing of each nucleic acid probe was conducted to rigorously demonstrate whether the desired characteristics discussed above could indeed be obtained, namely: 1) adequate exclusivity to all, even closely related, non-*E. coli* and Shigella organisms, 2) useful inclusivity patterns with respect to *E. coli* and Shigella strains, and 3) accessibility of the target regions under various assay conditions that might actually be employed. Because of the extremely large number of organisms potentially relevant to defining exclusivity (presently ca. 22 enteric genera, comprised of some 69 species and 29 unspeciated 'biogroups', Farmer et al., 1985) and inclusivity (five species and biogroups of Escherichia) characteristics of test probes, an iterative strategy was adopted to test and refine potential probes. The probes were conveniently synthesized by standard phosphoramidite (Caruthers, M. H. et al. [1983], in Gene Amplification and Analysis, eds. Papas, T. S., Rosenberg, M., Charikjian, J. G., Pub. Elsevier, New York, Vol. 3 pp.1-26) techniques on an Applied Biosystems instrument.

"Dot blot" analysis, in accordance with well known procedures, was employed to preliminarily test the inclusivity and exclusivity properties of these first generation probes. As is known, dot blot analysis generally involves immobilizing a nucleic acid or a population of nucleic acids on a filter such as nitrocellulose, nylon, or other derivatized membrane which can readily be obtained commercially, specifically for this purpose. Either DNA or RNA can be easily immobilized on such a filter and subsequently can be probed or tested for hybridization under any of a variety of nucleic acid hybridization conditions (i.e., stringencies) with nucleotide sequences or probes of interest. Under stringent conditions, probes whose nucleotide sequences have greater complementarity to the target sequence will exhibit a higher level of hybridization than probes containing less complementarity. For the oligonucleotide probes described herein, (i.e., 30-36 nucleotides in length) hybridization to rRNA targets at 60° C., for 14-16 hours (in a hybridization solution containing 0.9 M NaCl, 0.12 M Tris-HCl, pH 7.8, 6 mM EDTA, 0.1 M sodium phosphate buffer, 0.1% SDS, 0.1% pyrophosphate, 0.002% ficoll, 0.002% BSA, and 0.002% polyvinylpyrrolidine) followed by three, 15 minute post-hybridization washes at 60° C to remove unbound probes (in a solution containing 0.075 M NaCl, 0.0075 M NaCitrate, pH 7 and 0.1% SDS), would be sufficiently stringent to produce the levels of specificity and sensitivity demonstrated in the tables and examples. Techniques are also available in which DNA or RNA present in crude (unpurified) cell lysates can be immobilized without having to first purify the nucleic acid in question (referred to herein as cytodots, see for example Maniatis, T., Fritsch, E. F. and Sambrook, J. (1982) Molecular Cloning, a Laboratory Manual). This latter approach significantly decreases the amount of effort required to screen for particular nucleotide sequences which may be present in the nucleic acids of any particular organism and, moreover, is advantageously amenable to the mass screening of large numbers of organisms. It, therefore, is the method of choice for exclusivity and inclusivity screening of potential nucleic acid hybridization probes vs large numbers of organisms.

A list of non-*E. coli* bacteria which exemplify the type of bacteria that may be present in potentially *E. coli*-containing samples is given in Table 3. Note that these also represent many of the genera most closely related to *E. coli* and Shigella. As discussed above, a probe which demonstrates good exclusivity characteristics to such a broad representation of bacteria can reasonably be predicted to behave similarly to a much broader list of more distantly related enteric organisms.

Other considerations also affect optimal design characteristics of a probe sequence. One such is consideration of the geometry of the probe with respect to itself (i.e., intramolecular interactions). It has been discovered that potentially useful target region of 16S and 23S rRNAs most often are located in regions that exhibit a substantial possibility for self-complementary. As a result, probes to these regions can also exhibit self-complementary. Because potential interactions between the probe and target sequences are governed by the same types of parameters that govern the intramolecular annealing of the target or probe sequences to themselves, it is possible, particularly under solution hybridization conditions, that self-complementary probes can render themselves partially or completely inaccessible for hybridization to their target sequences. Thus, one important aspect of the probe design is to minimize such self-complementary. This necessitates making a compromise between maximum utilization of *E. coli*/Shigella-specific sequences and acceptable probe geometry.

The final steps of probe design and analysis ideally comprise testing real samples (e.g., food/clinical/environmental) and then selecting suitable probes for a final probe set so that the desirable properties are optimized under real assay conditions.

Probes

The foregoing probe selection strategy yielded a number of probes useful for identifying *E. coli* and/or Shigella bacteria in samples. As outlined in the Brief Description, Table 1 gives the probe sequences, aligned upon their target sites in the rRNAs of representative *E. coli* and Shigella strains. The "core" regions of nucleotide sequence differences within the target sites of *E. coli* and Shigella rRNA and representative non-*E. coli* and Shigella rRNA, which are the basis of the desirable discriminatory behavior of the probes, also are shown.

Two probes are shown in Table 1. Probe 683 is designed as a "detection" probe. Its usefulness, in conjunction with the capture probe 787 in a dual probe, liquid hybridization assay format, is described below in Example 1. The "capture probe", probe 787, is based upon the core region of sequence variability which is most useful for differentiating *E. coli* and Shigella from other enteric bacteria and is shown in Table 1. The optimal length and specific geometry of this probe are functions of the exact assay conditions in which it is to be employed, but any such "optimized" configuration would be based upon utilization of the *E. coli* plus Shigella "signature" sequence contained within the "core sequence". Probe 787 is capable of hybridizing with exceptional inclusivity and exclusivity behavior to all *E. coli* and Shigella and no other bacteria, under appropriate conditions such as those described herein. Under other assay conditions, shorter or longer versions of probe 787 might be more optimal but, as a practical matter, would be no more than trivial refinements of the basic probe sequence.

Table 2 shows the hybridization behavior of the probes toward nucleic acid targets from representative species of *E. coli* and Shigella. Note that, based upon the dot blot data (using P-32 labeled probe as described above), probe 787 hybridizes to (is inclusive for) all *E. coli* strains in our collection including strains categorized as "normal" (i.e. isolated from apparently healthy humans), toxogenic, invasive, inactive, enteropathogenic, and atypical. It also is fully inclusive for all Shigella including strains of *S. dysenteriae, S. sonnei. S. boydii, S. flexneri,* and even the biochemically and genetically distinct strain *S. boydii* C13. This behavior demonstrates a very close genetic relationship between *E. coli* and Shigella, even to the exclusion of other named species of Escherichia such as *E. vulneris, E. blattae* and *E. hermanii*. These non-coli strains of Escherichia should, by this phylogenetic criterion, be transferred to a genus other than Escherichia. *E. fergusonii,* on the other hand, would appear to be appropriately classified as a specific relative of the *E. coli*/Shigella "supergenus". Results of liquid hybridization experiments, described below but also shown in Table 2, further extended the inclusivity profile of probe 787 to include additional clinical and food isolates of *E. coli*.

Table 3 shows the hybridization behavior of the probes in dot blots and in liquid hybridization experiments versus various non-*E. coli* and non-Shigella bacteria. In the dot blot experiment, probe 787 was radioactively labeled with phosphorous-32 for detection and quantitation. Little or no cross-hybridization of the probe was observed under the hybridization conditions employed in this experiment to any non-*E. coli* or Shigella bacteria. These conditions comprised hybridizing at 60° C. for 14–16 hours in the hybridization solution previously described. In addition to the organisms listed in Table 3, probe 787 was tested versus 350 strains and isolates of Salmonella, none of which should detectable hybridization. Similar results are obtained in liquid hybridization experiments using probes 787 and 683 (in combination) versus various non-*E. coli* and non-Shigella bacterial (Example 1 - General).

EXAMPLE 1 - General

A Homopolymer Capture, Dual Probe, Liquid Hybridization Format

Cultures containing *E. coli* and/or non-*E. coli* bacteria are grown in appropriate broth, then the nucleic acids are released by any of a number of appropriate lysis agents (e.g., NaOH, guanidine salts, detergent, enzymatic treatment, or some combination of the aforementioned). Mechanical disruption of the bacteria (e.g., French press, sonication, etc.) also would be appropriate. Hybridization is carried out with two different probes or probe sets that recognize the same rRNA subunit molecule, at least one of which, but not necessarily both, must be specific for the organism to be detected. In this example, the *E. coli* /Shigella-specific "capture" probe 787 is enzymatically tailed with 20–200 deoxyadenosine (dA) residues at its 3' terminus, and the reporter probe, designated probe 683, is labeled either chemically or enzymatically with radioactive phosphorous (P-32) or another small ligand (such as fluorescein or biotin, the latter being used in the liquid hybridization experiments recorded in Tables 2 and 3-Example 1, General, and the former being used in the experiment described in Table 4 - Example 1, Specific) which is used to detect the captured target molecules.

Generally, following cultivation/enrichment, bacteria present in the test samples are transferred in small aliquots to test tubes. For the tested Shigella cultures, aliquots of 100-fold dilutions of overnight broth cultures as well as aliquots of undiluted cultures were assayed (Table 2). The bacteria are lysed, the capture and reporter probes are added, and hybridization is allowed to proceed in an appropriate solution at an appropriate temperature such as those already described. The solution containing the target/probe complex then is brought into contact with a surface containing bound deoxythymidine (dT) homopolymer 15–3000 nucleotides in length, under conditions that will allow hybridization between the dA "tail" on the capture probe and the immobilized dT. In this example, the dT is bound to a plastic "dipstick" which is submerged in the Lysis/hybridization solution. If *E. coli* /Shigella ribosomal RNA was present in the test sample, the dA tailed, *E. coli/*-Shigella-specific capture probes would have hybridized to the target rRNA sequences present and, in turn, would be captured onto the dipstick. Unhybridized nucleic acids and cellular debris are washed away, leaving the captured DNA-RNA complex attached to the surface via the dA-dT duplex. The reporter probe also is bound to the dipstick via the chain of interactions—Capture surface-dT: dA-Capture probe:Target:-Reporter Probe—only if the correct target nucleic acid is present. The bound, ligand-derivatized (i.e., biotinylated in this example) reporter probe then is detected by the addition of a ligand-binding enzyme complex (i.e., streptavidin-horseradish peroxidase in the present example). Following incubation under conditions permitting specific binding of the detection complex, washing to remove non-bound enzyme, addition of chromogenic substrate and subsequent color development (typically 20–30 minutes), and the optional addition of color-termination solution, the developed color is measured colorimetrically. This reading (typically in the range of 0.2→2.0 absorbance units) is compared to the negative control levels, a threshold or cutoff value is established, and a determination of the "significance" of the experimental levels is made. Tables 2 and 3 show the results of one such experiment, using pure culture of various *E. coli* (Table 2) and non-*E. coli* (Table 3) bacteria (Example 1, General).

As can be seen in Table 2, more than 120 *E. coli* strains and 38 Shigella strains were tested. Compared with the MUG test, the liquid hybridization assay detects all strains. The MUG test missed at least one third of the tested *E. coli* strains. Specifically, the MUG test did not detect all enteropathogenic *E. coli* serotype 0157 strains.

Table 3 (exclusivity data) shows results from cultures of 168 strains of non-*E. coli* /Shigella tested using the liquid hybridization assay (Example 1, General). All tested strains were negative. Most absorbance values were below 0.1 units, with absolute background (media blank) being 0.07 units.

EXAMPLE 1 - SPECIFIC 50 g of food sample was homogenized in 450 ml of Butterfield's phosphate-buffered diluent (as per BAM-/AOAC recommendation) and then 3.0 ml of this homogenate was transferred to 30 ml of primary enrichment broth (lauryl sulfate tryptose broth [LST], 20 g tryptose or trypticase, 5.0 g NaCl, 5.0 g lactose, 2.75 g $K_2HPO_4$, 2.75 g $KH_2PO_4$ and 0.1 g Na-lauryl sulfate in 1 liter $H_2O$). The inoculated LST was then incubated in a bottle for 24±2 hours at 35° C. Following this primary enrichment step a secondary enrichment step was performed. The primary enrichment culture was mixed well; 0.1 ml of the primary enrichment culture was transferred to a test tube or bottle containing 10 ml of secondary enrichment broth (e.g., LST broth), and incubated for 24±2 hours at 35° C. 0.50 ml of secondary enrichment broth culture then was treated with 0.10 ml of lysis solution (containing NaOH, 0.75 N) by incubation at room temperature (15°-25° C.) for five minutes. The bacterial lysates were neutralized with the addition of 0.1 ml of neutralization buffer (containing 4M $KH_2PO_4:Na_2HPO_4$, 2:1).

The presence of target E. coli nucleic acids in each sample was detected by addition of 0.10 ml of the specific capture and detector probe sets (containing between 2.8–5.6 microgram/ml of preferred capture probe 787., and, 4–8 microgram/ml of detector probe 683 labeled at its termini with fluorescein, in this example). A set of dT coated capture dipsticks were placed into the test tubes containing the bacterial lysates and the specific probe sets. The contents were incubated in a 65° C water bath for 60 minutes to enable hybridization of specific capture and reporter probes to target nucleic acids and the capture of these specific DNA/rRNA hybrids to the dipsticks.

After hybridization, the dipsticks were washed for one minute by immersing the dipsticks in a wash basin containing enough wash solution (50 mM Tris, pH 7.5, 150 mM NaCl, 2 mM EDTA, and 0.1% Tween 20) to cover the dT-coated portion of the dipstick. This process was then repeated in fresh wash solution.

The washed dipsticks were removed from the wash basin, blotted with absorbent paper to remove excess wash buffer, placed into a set of test tubes containing 0.75 ml of an antibody-enzyme conjugate (anti-fluorescein conjugated with horse radish peroxidase, in this example, diluted in wash buffer), and allowed to incubate at room temperature for 20 minutes.

After allowing the antigen-antibody reaction to occur, the dipsticks were removed from the test tubes, washed and blotted in the same manner as described in the preceding two paragraphs. The dipsticks were placed into a set of test tubes containing substrate-chromogen mixtures and allowed to incubate at room temperature for ten minutes. The dipsticks then were removed and the color development step in the assay tubes terminated by the addition of 0.25 ml 4N sulfuric acid. The absorbance of the samples at 450 nanometers was measured with a spectrophotometer (referred to as A450).

Generally, the average of three negative control samples (prepared from ca. $10^8$ formaldehyde-killed *Yersinia enterocolitica*) were obtained and a value equal to 2.5 times the average A450 of the three negative controls was chosen as the cutoff value. Sample tubes with higher A450 values were considered positive for *E. coli*/Shigella, those with lower A450 values were considered negative for *E. coli* /Shigella. Results are shown in Table 4. With experience we have found that A450 values of 0.2 and above constitute positive results for the presence of *E. coli* and/or Shigella.

As can be seen in Table 4, 20 out of 30 food samples were inoculated with different *E. coli* strains at various inoculation levels. All 20 of the inoculated food samples were detected by the non-isotopic hybridization assay after 48 hours of incubation. Those hybridization positive food samples also were evaluated and confirmed by standard microbiological confirmation methods.

While the description of the invention has been made with reference to detecting rRNA, it will be readily understood that the probes described herein and probes complementary to those described herein also will be useful to detect the genes (DNA) encoding the rRNA and accordingly, such probes are to be deemed derivatives of the described probes and encompassed within the spirit and scope of the present invention and the appended claims.

TABLE 1

| *ESCHERICHIA COLI* CORE AND PROBE SEQUENCE INFORMATION | |
|---|---|
| 16S rRNA Position # | 405 ↓                                                            455 ↓ |
| *Proteus vulgaris* | ... UGUAUGAAGAAGGCCUUAGGGUUGUAAAGUACUUUCAGCGGGGAGGAAGGU <br>                          477                 490 <br>                          ↓                    ↓ <br> GAUAAAGUUAAUACCUUUGUCAAUUGACGUUACCC ... |
| *Yersinia enterocolitica* | ... UGUGUGAAGAAGGCCUUCGGGUUGUAAAGCACUUUCAGCGAGGAGGAAGGC <br> CAAUAACUUAAUACGUUGUUGGAUUGACGUUACUC ... |
| *Salmonella typhimurium* | ... UGUAUGAAGAAGGCCUUCGGGUUGUAAAGUACUUUCAGCGGGGAGGAAGGU <br> GUUGUGGUUAAUAACCGCAGCAAUUGACGUUACCC ... |
| *Sh. dysenteriae* | ... UGUAUGAAGAAGGCCUUCGGGUUGUAAAGUACUUUCNNCGGGGAGGAAGGG <br> AGUAAAGUUAAUACCUUUGCUCAUUGANYUUACCC ... |
| *Sh. boydii* C13 | ... UGUAUGAAGAAGGCCUUCGGGUUGUAAAGUACUUUCANCGGGGAGGAAGGG <br> AGUAAAGUUAAUAGCUUUGCUNAUUGACGUUACCC ... |
| *E. coli* "atypical" | ... UGUAUGAAGAAGGCCUUCGGGUUGUAAAGUACUUUCNNCGGGGAGGAAGGG <br> AGUAAAGUUAAUACCUUUGCUYAUUGACGUUACCC ... |
| *E. coli* "alkalescens" | ... UGUAUGAAGAAGGCCUUCGGGUUGUAAAGUACUUUCNNCGGGGAGGAAGGG <br> AGUAAAGUUAAUACCUUUGCUYAUUGACGUUACCC ... |
| Probe 683 | ccATACTTCTTCCGGAAGCCCAACATTTCATGAAAGTcc-5' |
| *E. coli* "normal" | ... UGUAUGAAGAAGGCCUUCGGGUUGUAAAGUACUUUCAGCGGGGAGGAAGGG <br> AGUAAAGUUAAUACCUUUGCUCAUUGACGUUACCC ... |
| Core Variation | GAGUAAAGUUAAUACCUUUGCUC |
| Probe 787 | TCCTTCCCTCATTTCAATTATGGAAACGAGTAACT-5' |

TABLE 2

| *E. COLI* & SHIGELLA - INCLUSIVITY DATA | | | | | | |
|---|---|---|---|---|---|---|
| | | | Dot Blot Hybrid. Index | MUG TEST (72 hr.) | | Example 1 General |
| *E. coli* type | Strain | Source | Probe 787 | Gas | Fluor | A450 |
| "NORMAL" | | | | | | |
| " | 3116 | (4) | + + + + | + | + | 1.70 |
| " | 3117 | (4) | + + + + | + | + | 1.56 |
| " | 3121 | (4) | + + + + | + | − | 2.05 |
| " | 3122 | (4) | + + + + | + | + | 1.67 |

TABLE 2-continued
E. COLI & SHIGELLA - INCLUSIVITY DATA

| | | | | | | |
|---|---|---|---|---|---|---|
| " | 3124 | (4) | +++++ | + | + | 2.07 |
| " | 3125 | (4) | +++++ | + | + | 1.86 |
| " | 3126 | (4) | +++++ | + | + | 1.97 |
| " | 3128 | (4) | +++++ | + | + | 1.67 |
| " | 3130 | (4) | +++++ | + | + | 1.60 |
| " | 3131 | (4) | +++++ | + | + | 1.30 |
| " | 3133 | (4) | +++++ | + | + | 1.85 |
| " | 3135 | (4) | +++++ | + | + | 1.94 |
| " | 3139 | (4) | +++++ | + | + | 1.90 |
| " | 3148 | (4) | +++++ | + | − | 1.98 |
| " | 3150 | (4) | +++++ | + | + | 1.91 |
| " | 3153 | (4) | +++++ | + | + | 2.0 |
| " | 3158 | (4) | +++++ | + | − | 2.02 |
| " | 3161 | (4) | +++++ | + | + | 1.41 |
| "TOXIGENIC" | | | | | | |
| " | 3118 | (4) | +++++ | + | + | 1.79 |
| " | 3119 | (4) | +++++ | + | − | 1.52 |
| " | 3120 | (4) | +++++ | + | + | 2.10 |
| " | 3123 | (4) | +++++ | + | − | 2.15 |
| " | 3127 | (4) | +++++ | + | + | 2.08 |
| " | 3129 | (4) | +++++ | + | + | 1.76 |
| " | 3132 | (4) | +++++ | + | + | 1.60 |
| " | 3134 | (4) | +++++ | + | − | 2.10 |
| " | 3136 | (4) | +++++ | + | + | 2.04 |
| " | 3142 | (4) | +++ | + | − | 2.12 |
| " | 3147 | (4) | ++ | + | + | 2.04 |
| " | 3151 | (4) | +++++ | + | + | 1.94 |
| " | 3154 | (4) | +++++ | + | − | 1.87 |
| " | 3156 | (4) | +++++ | + | + | 2.05 |
| " | 3158 | (4) | +++++ | + | + | 2.2 |
| " | 3160 | (4) | +++++ | + | + | 2.05 |
| "INVASIVE" | | | | | | |
| " | 3138 | (4) | +++++ | + | − | 1.85 |
| " | 3141 | (4) | +++++ | + | + | 1.76 |
| " | 3145 | (4) | +++ | + | + | 0.78 |
| " | 3146 | (4) | +++++ | +/− | + | 1.45 |
| " | 3157 | (4) | +++++ | + | + | 1.22 |
| " | 3037 | (5) | +++++ | + | + | 1.12 |
| B "INACTIVE" | | | | | | |
| " | 3045 | (6) | +++++ | + | + | 0.76 |
| " | 3049 | (6) | ND | − | + | ND |
| " | 3050 | (6) | +++++ | + | + | 1.34 |
| "ENTEROPATHOGENIC-0157 H7" | | | | | | |
| " | 3137 | (4) | +++++ | + | − | 2.05 |
| " | 3140 | (4) | +++++ | + | − | 2.0 |
| " | 3143 | (4) | +++++ | + | − | 1.85 |
| " | 3144 | (4) | +++++ | + | − | 2.02 |
| " | 3152 | (4) | +++++ | + | − | 1.92 |
| " | 3155 | (4) | +++++ | + | − | 1.61 |
| " | 3162 | (4) | +++++ | + | − | 2.05 |
| " | 3163 | (4) | +++++ | + | − | 1.95 |
| " | 3164 | (4) | +++++ | + | − | 2.0 |
| " | 3165 | (4) | +++++ | + | − | 1.72 |
| " | 3040 | (5) | +++ | + | − | 1.88 |
| "ENTEROPATHOGENIC-non0157" | | | | | | |
| " | 3038 | (5) | +++ | + | + | 2.0 |
| " | 3039 | (5) | +++++ | + | + | 2.1 |
| " | 3041 | (5) | +++++ | + | + | 1.7 |
| " | 3042 | (5) | +++++ | + | + | 1.2 |
| " | 3043 | (5) | +++ | + | + | 1.8 |
| " | 839 | (4) | ++ | + | + | 2.1 |
| " | 840 | (7) | +++ | + | + | 1.5 |
| " | 841 | (7) | +++++ | + | − | 2.3 |
| " | 842 | (7) | +++++ | + | + | 1.9 |
| " | 843 | (7) | +++++ | + | + | 1.4 |
| " | 844 | (7) | +++++ | + | + | 1.5 |
| " | 845 | (7) | +++++ | + | + | 2.0 |
| " | 846 | (4) | ++ | − | + | 1.5 |
| " | 847 | (4) | +++ | + | + | 1.5 |
| " | 848 | (4) | +++++ | + | − | 1.07 |
| " | 3149 | (4) | +++++ | + | + | 0.63 |
| "ALKALESCENS DISPAR" | | | | | | |
| " | 3066 | (1) | +++++ | − | + | 0.39 |
| "ATYPICAL" | | | | | | |
| " | 833 | (2) | +++++ | − | + | 0.35 |
| " | 834 | (2) | +++++ | − | + | 0.16 |
| Flour 1 | 074 | (3) | ND | + | + | 0.53 |
| Flour 2 | 075 | (3) | ND | + | + | 0.54 |
| Cheese 1 | 076 | (3) | ND | + | − | 0.86 |
| Cheese 2 | 077 | (3) | ND | + | + | 0.72 |
| Cheese 1 | 078 | (17) | ND | + | + | 1.03 |

TABLE 2-continued

E. COLI & SHIGELLA - INCLUSIVITY DATA

| | | | | | | |
|---|---|---|---|---|---|---|
| Cheese 2 | 079 | (17) | ND | + | + | 1.15 |
| Soy Strain Clinical | 102 | (1) | ND | + | + | 1.85 |
| " | 102149 | (8) | ND | + | + | 1.26 |
| " | 102565 | (8) | ND | + | + | 1.12 |
| " | 103834 | (8) | ND | + | + | 0.75 |
| " | 103965 | (8) | ND | + | + | 1.31 |
| " | 103010 | (8) | ND | + | − | 1.60 |
| " | 102826 | (8) | ND | + | + | 1.84 |
| " | 102994 | (8) | ND | + | + | 0.66 |
| " | 102627 | (8) | ND | + | − | 1.4 |
| " | 102765 | (8) | ND | + | + | 1.21 |
| " | 102641 | (8) | ND | + | + | 1.47 |
| " | 102109 | (8) | ND | + | + | 0.63 |
| " | 102005 | (8) | ND | + | − | 1.02 |
| " | 102075 | (8) | ND | + | + | 0.73 |
| " | 104114 | (8) | ND | + | + | 1.14 |
| " | 103280 | (8) | ND | + | − | 0.09* |
| " | 102520 | (8) | ND | − | + | 0.51 |
| " | 102761 | (8) | ND | + | + | 0.53 |
| " | 102613 | (8) | ND | + | − | 1.24 |
| " | 102762 | (8) | ND | + | + | 1.37 |
| " | 103054 | (8) | ND | − | + | 0.48 |
| " | 103129 | (8) | ND | + | + | 0.64 |
| " | 102907 | (8) | ND | + | + | 0.62 |
| " | 102525 | (8) | ND | + | + | 0.08* |
| " | 102886 | (8) | ND | + | − | 1.86 |
| " | 104007 | (8) | ND | + | − | 0.38 |
| " | 102687-1 | (8) | ND | + | + | 1.17 |
| " | 102024 | (8) | ND | + | + | 1.78 |
| " | 102149 | (8) | ND | − | + | 2.1 |
| " | 102911-3 | (8) | ND | − | + | 2.2 |
| " | 103584 | (8) | ND | − | + | 0.6 |
| " | 102374 | (8) | ND | + | + | 0.91 |
| " | 102706 | (8) | ND | + | + | 1.48 |
| " | 103133-1 | (8) | ND | + | + | 0.69 |
| " | 102718 | (8) | ND | + | − | 1.98 |
| " | 103580 | (8) | ND | + | + | 0.44 |
| " | 103603 | (8) | ND | + | + | 1.15 |
| " | 102979 | (8) | ND | + | + | 0.89 |
| " | 102687-1 | (8) | ND | + | + | 0.68 |
| " | 103765 | (8) | ND | + | + | 1.44 |
| " | 102458 | (8) | ND | + | + | 1.33 |
| " | 103691 | (8) | ND | + | + | 1.33 |
| " | 103666 | (8) | ND | + | + | 1.26 |
| " | 103083 | (8) | ND | + | + | 0.53 |
| " | 103000-2 | (8) | ND | − | + | 0.77 |
| " | 101544 | (8) | ND | + | − | 1.98 |
| " | 103253 | (8) | ND | − | − | 0.80 |
| " | 103327 | (8) | ND | + | + | 1.70 |
| " | 102121 | (8) | ND | + | + | 2.2 |
| " | 102386 | (8) | ND | + | + | 1.37 |
| E. vulneris | 3047 | (6) | − | − | − | 0.04 |
| " | 836 | (2) | − | − | − | 0.04 |
| E. fergusonii | 3044 | (6) | +++ | − | − | 2.2 |
| " | 3051 | (6) | ++++ | − | − | 2.2 |
| E. blattae | 3052 | (6) | − | − | − | 0.03 |
| E. hermanii | 835 | (2) | − | − | − | 0.07 |

| | | | | Example 1 General ($A_{450}$) | |
|---|---|---|---|---|---|
| Shigella species | GTS Strain | Source | Hybrid. Index Probe 787 | 1:100 dilution | undiluted |
| S. dysenteriae | RF970 | (2) | ++++ | 1.02 | 2.08 |
| " | RF952 | (9) | ++++ | ND | ND |
| S. dysenteriae, 2 | IG774 | (9) | ++++ | ND | ND |
| S. dysenteriae, TET | IG703 | (16) | ++++ | ND | ND |
| S. dysenteriae, TET | IG704 | (16) | ++++ | ND | ND |
| S. dysenteriae, TET | IG705 | (16) | ++++ | ND | ND |
| S. dysenteriae, TET | IG710 | (15) | ++++ | ND | ND |
| " | IG725 | (16) | ++++ | ND | ND |
| " | IG726 | (2) | ++ | ND | ND |
| S. dysenteriae, 4 | IG824 | (13) | ++++ | ND | ND |
| " | IG826 | (13) | ++++ | ND | ND |
| " | IG828 | (13) | ++++ | ND | ND |
| S. dysenteriae, 3 | IG861 | (6) | ++++ | 1.00 | 2.08 |
| S. dysenteriae, 4 | IG862 | (6) | ++++ | 1.20 | 2.06 |
| S. dysenteriae, 5 | IG863 | (6) | ++++ | 0.81 | 2.05 |
| S. dysenteriae, 6 | IG864 | (6) | ++++ | 1.14 | 2.06 |
| S. dysenteriae, 7 | IG865 | (6) | ++++ | 0.79 | 1.99 |
| S. dysenteriae, 8ab | IG866 | (6) | ++++ | 0.69 | 2.01 |
| S. dysenteriae, A9 | IG867 | (6) | ++++ | 1.10 | 2.01 |

TABLE 2-continued
E. COLI & SHIGELLA - INCLUSIVITY DATA

| | | | | | |
|---|---|---|---|---|---|
| S. dysenteriae, 10 | IG868 | (6) | ++++ | 1.03 | 2.01 |
| S. dysenteriae, 3 | IG940 | (11) | ++++ | ND | ND |
| S. dysenteriae, 3 | IG941 | (11) | ++++ | ND | ND |
| S. dysenteriae, 4 | IG942 | (11) | ++++ | ND | ND |
| S. dysenteriae, 9 | IG943 | (11) | ++++ | ND | ND |
| S. dysenteriae, 9 | IG944 | (11) | ++++ | ND | ND |
| S. sonnei | RF968 | (2) | ++++ | ND | ND |
| " | RF943 | (9) | ++++ | ND | ND |
| " | RF949 | (9) | ++++ | ND | ND |
| " | IG781 | (9) | ++++ | ND | ND |
| " | IG722 | (14) | ++++ | ND | ND |
| " | IG722 | (14) | ++++ | ND | ND |
| " | IG781 | (9) | ++++ | ND | ND |
| " | IG722 | (14) | ++++ | ND | ND |
| " | IG723 | (14) | ++++ | ND | ND |
| " | IG713 | (15) | ++++ | 0.55 | 1.93 |
| " | IG714 | (15) | ++++ | ND | ND |
| " | IG720 | (15) | ++++ | ND | ND |
| " | IG719 | (15) | ++++ | ND | ND |
| " | IG721 | (15) | ++++ | ND | ND |
| " | IG712 | (15) | ++++ | ND | ND |
| " | IG707 | (15) | ++++ | ND | ND |
| " | IG708 | (15) | ++++ | ND | ND |
| " | IG709 | (15) | ++++ | ND | ND |
| " | IG711 | (15) | ++++ | ND | ND |
| " | IG715 | (15) | ++++ | ND | ND |
| " | IG831 | (2) | ++++ | 0.44 | 1.90 |
| " | IG830 | (2) | ++++ | ND | ND |
| " | IG731 | (12) | ++++ | 0.93 | 1.98 |
| " | IG730 | (12) | ++++ | ND | ND |
| " | IG733 | (12) | ++++ | ND | ND |
| " | IG728 | (12) | ++++ | ND | ND |
| " | IG732 | (12) | ++++ | ND | ND |
| " | IG729 | (12) | ++++ | ND | ND |
| " | IG734 | (12) | ++++ | ND | ND |
| " | IG727 | (2) | ++++ | ND | ND |
| " | IG827 | (13) | ++++ | ND | ND |
| " | IG821 | (13) | ++++ | ND | ND |
| " | IG869 | (6) | ++++ | ND | ND |
| " | IG870 | (6) | ++++ | ND | ND |
| " | IG929 | (1) | ++++ | ND | ND |
| " | IG930 | (11) | ++++ | 0.84 | 1.98 |
| " | IG931 | (11) | ++++ | ND | ND |
| " | IG932 | (11) | ++++ | ND | ND |
| " | IG933 | (11) | ++++ | ND | ND |
| " | IG934 | (11) | ++++ | ND | ND |
| " | IG951 | (10) | ++++ | ND | ND |
| " | IG952 | (10) | ++++ | ND | ND |
| " | IG953 | (10) | ++++ | ND | ND |
| " | IG954 | (10) | ++++ | ND | ND |
| " | IG955 | (10) | ++++ | ND | ND |
| " | IG956 | (10) | ++++ | 0.49 | 1.88 |
| " | IG957 | (10) | ++++ | ND | ND |
| " | IG958 | (10) | ++++ | ND | ND |
| " | IG959 | (10) | ++++ | ND | ND |
| " | IG960 | (10) | ++++ | ND | ND |
| " | IG961 | (10) | ++++ | 0.61 | 1.98 |
| " | IG962 | (10) | ++++ | ND | ND |
| " | IG963 | (10) | ++++ | ND | ND |
| " | IG964 | (10) | ++++ | ND | ND |
| " | IG965 | (10) | ++++ | ND | ND |
| " | IG966 | (10) | ++++ | ND | ND |
| " | IG967 | (10) | ++++ | ND | ND |
| " | IG968 | (10) | ++++ | ND | ND |
| " | IG969 | (10) | ++++ | ND | ND |
| " | IG970 | (10) | ++++ | 0.51 | 1.98 |
| " | IG971 | (10) | ++++ | ND | ND |
| " | IG972 | (10) | ++++ | ND | ND |
| " | IG973 | (10) | ++++ | ND | ND |
| " | IG974 | (10) | ++++ | ND | ND |
| " | IG975 | (10) | ++++ | ND | ND |
| " | IG976 | (10) | ++++ | ND | ND |
| " | IG979 | (1) | ++++ | ND | ND |
| " | IG980A | (1) | ++++ | ND | ND |
| " | IG980B | (1) | ++++ | ND | ND |
| " | IG982 | (1) | ++++ | ND | ND |
| S. flexneri, 2A | RF973 | (2) | ++++ | 0.50 | 1.95 |
| " | RF951 | (9) | ++++ | ND | ND |
| " | RF944 | (9) | ++++ | ND | ND |
| " | RF946 | (9) | ++++ | ND | ND |
| " | RF947 | (9) | ++++ | ND | ND |

TABLE 2-continued
E. COLI & SHIGELLA - INCLUSIVITY DATA

|  |  |  |  |  |  |
|---|---|---|---|---|---|
| " | RF950 | (9) | ++++ | ND | ND |
| " | IG763 | (9) | ++++ | ND | ND |
| " | IG764 | (9) | ++++ | ND | ND |
| " | IG765 | (9) | ++++ | ND | ND |
| " | IG766 | (9) | ++++ | ND | ND |
| " | IG767 | (9) | ++++ | ND | ND |
| " | IG768 | (9) | ++++ | ND | ND |
| " | IG770 | (9) | ++++ | ND | ND |
| " | IG771 | (9) | ++++ | ND | ND |
| " | IG772 | (9) | ++++ | ND | ND |
| " | IG773 | (9) | ++++ | ND | ND |
| " | IG775 | (9) | ++++ | ND | ND |
| " | IG777 | (9) | ++++ | ND | ND |
| " | IG778 | (9) | ++++ | ND | ND |
| " | IG782 | (9) | ++++ | ND | ND |
| " | IG724 | (14) | ++++ | ND | ND |
| S. flexneri, 2B | IG716 | (2) | ++++ | 0.43 | 1.99 |
| " | IG743 | (12) | ++++ | ND | ND |
| " | IG744 | (12) | ++++ | ND | ND |
| " | IG737 | (12) | ++++ | ND | ND |
| " | IG735 | (12) | ++++ | ND | ND |
| " | IG738 | (12) | ++++ | ND | ND |
| S. flexneri | IG736 | (12) | ++++ | ND | ND |
| " | IG741 | (12) | ++++ | ND | ND |
| " | IG740 | (12) | ++++ | ND | ND |
| " | IG739 | (12) | ++++ | ND | ND |
| " | IG742 | (16) | ++++ | ND | ND |
| S. flexneri, 3 | IG825 | (13) | ++++ | ND | ND |
| " | IG817 | (13) | ++++ | ND | ND |
| S. flexneri, 1B | IG818 | (13) | ++++ | ND | ND |
| S. flexneri, HYB | IG819 | (13) | ++++ | ND | ND |
| " | IG820 | (13) | ++++ | ND | ND |
| " | IG822 | (13) | ++++ | ND | ND |
| S. flexneri, 4 | IG838 | (13) | ++++ | ND | ND |
| S. flexneri, 6 | IG871 | (6) | ++++ | ND | ND |
| S. flexneri, 5 | IG872 | (6) | ++++ | ND | ND |
| S. flexneri, 4B | IG873 | (6) | ++++ | 0.39 | 1.93 |
| S. flexneri, 4A | IG874 | (6) | ++++ | ND | ND |
| S. flexneri, 3C | IG875 | (6) | ++++ | ND | ND |
| S. flexneri, 3B | IG876 | (6) | ++++ | 1.10 | 1.68 |
| S. flexneri, 3A | IG877 | (6) | ++++ | ND | ND |
| S. flexneri, 1B | IG878 | (6) | ++++ | ND | ND |
| S. flexneri, 1A | IG879 | (6) | ++++ | ND | ND |
| S. flexneri, 1A | IG945 | (11) | ++++ | 0.26 | 1.88 |
| S. flexneri, 18 | IG946 | (11) | ++++ | 0.22 | 1.92 |
| S. flexneri, 3A | IG947 | (11) | ++++ | 0.26 | 1.89 |
| S. flexneri, 4A | IG948 | (11) | ++++ | 0.25 | 1.83 |
| S. flexneri, 5 | IG949 | (11) | ++++ | 0.39 | 1.94 |
| S. flexneri, 6 | IG950 | (11) | ++++ | 0.92 | 2.00 |
| S. boydii, 2 | RF971 | (2) | ++++ | 0.69 | 2.01 |
| S. boydii, C13 | RF974 | (2) | ++++ | ND | ND |
| " | RF948 | (9) | ++++ | ND | ND |
| S. boydii, 17 | IG701 | (6) | ++++ | ND | ND |
| S. boydii, 18 | IG702 | (6) | ++++ | ND | ND |
| S. boydii, 16 | IG700 | (6) | ++++ | ND | ND |
| " | IG718 | (14) | ++++ | ND | ND |
| S. boydii, 1 | IG832 | (2) | ++++ | 0.69 | 2.00 |
| S. boydii, 9 | IG829 | (13) | ++++ | ND | ND |
| S. boydii, 3 | IG880 | (6) | ++++ | 0.72 | 1.99 |
| S. boydii, 5 | IG882 | (6) | ++++ | ND | ND |
| S. boydii, 6 | IG883 | (6) | ++++ | 1.04 | 2.02 |
| S. boydii, 7 | IG884 | (6) | ++++ | 0.13 | 1.90 |
| S. boydii, 8 | IG885 | (6) | ++++ | 0.84 | 2.02 |
| S. boydii, 9 | IG886 | (6) | ++++ | 0.45 | 1.98 |
| S. boydii, 10 | IG887 | (6) | ++++ | 0.99 | 2.01 |
| S. boydii, 11 | IG888 | (6) | ++++ | 0.31 | 1.96 |
| S. boydii, 12 | IG889 | (6) | ++++ | ND | ND |
| S. boydii, 13 | IG890 | (6) | ++++ | 0.21 | 1.81 |
| S. boydii, 14 | IG891 | (6) | ++++ | 0.95 | 2.02 |
| S. boydii, 15 | IG892 | (6) | ++++ | 0.37 | 2.01 |
| S. boydii, 4 | IG935 | (11) | ++++ | ND | ND |
| S. boydii, 5 | IG936 | (11) | ++++ | ND | ND |
| S. boydii, 10 | IG937 | (11) | ++++ | ND | ND |
| S. boydii, 11 | IG938 | (11) | ++++ | ND | ND |
| S. boydii, 14 | IG939 | (11) | ++++ | ND | ND |

*Confirmed biochemically as *Citrobacter freundii*, not *E. coli*
Key for dot blot hybridization:
++++ = positive control level of hybridization
+++ = strong hybridization
++ = weak but readily detectable

TABLE 2-continued
E. COLI & SHIGELLA - INCLUSIVITY DATA

+ = barely detectable
− = zero
ND = not determined
Key for MUG test:
+ = detectable
+/− = equivocal
− = not detectable
Gas = detectable gas formation in lactose-containing broth - an indication characteristic (for E. coli) of fermentation of this sugar
Fluorescence (Fluor) = the appearance of fluorescence under long-wave UV light (emission, about 366 nm). The fluorescence comes from hydrolyzing the compound 4-methylumbelliferyl-$\beta$-D-glucuronide (MUG) by $\beta$-glucuronidase in E. coli.
Source key:
(1) GENE-TRAK Systems, Framingham, MA.
(2) American Type Culture Collection, Bethesda, MD.
(3) Silliker Laboratories, Chicago, Illinois
(4) Grace Thorne, Boston Children's Hospital
(5) Steven Moseley, Seattle Children's Hospital
(6) K. Wachsmuth, CED, Atlanta
(7) Richard Hull, Baylor college of Medicine, Houston TX.
(8) Massachusetts General Hospital
(9) Gary Doern, Universitiy of Mass. Medical Center
(10) Don Goldmann, Boston Children's Hospital
(11) Susan Gibson, Texas Health Department
(12) Madigan Army Medical Center
(13) Samuel Formal, Walter Reed Army Institute of Research
(14) Ellen Crotty, University Hospital, Cleveland
(15) Thomas Gavan, Cleveland Clinic Foundation
(16) C. W. Shuster, Case Western Reserve University
(17) Deibel Laboratory, Madison, WI

TABLE 3
E. COLI & SHIGELLA - EXCLUSIVITY DATA

| Genus. species | Strain | Source | Dot Blot (p787) | Example 1 General A 450 nm |
|---|---|---|---|---|
| Escherichia coli | N99 | (1) | + + + + | 1.20 Positive Control |
| Acinetobacter calcoaceticus | 115 | (1) | ND | 0.06 |
| Acinetobacter calcoaceticus | ATCC19606 | (2) | ND | 0.06 |
| Aeromonas hydrophilia | ATCC7965 | (2) | ND | 0.05 |
| Aeromonas sobria | IG837 | (1) | ND | 0.05 |
| Alcaligenes denitrificans | ATCC27062 | (2) | ND | 0.05 |
| Alteromonas putrifaciens | ATCC8071 | (2) | − | ND |
| Bacillus cereus | ATCC14579 | (2) | ND | 0.05 |
| Candida albicans | ATCC18804 | (2) | ND | 0.06 |
| Candida galbrata | ATCC20014 | (2) | ND | 0.06 |
| Citrobacter amalonaticus | 9020-77 | (18) | − | ND |
| Citrobacter amalonaticus | ATCC25406 | (2) | − | ND |
| Citrobacter amalonaticus | ATCC25405 | (2) | − | ND |
| Citrobacter diversus | ATCC13048 | (2) | ND | 0.04 |
| Citrobacter diversus | S122B | (3) | − | ND |
| Citrobacter diversus | 3613-63 | (18) | − | ND |
| Citrobacter diversus | ATCC22156 | (2) | − | ND |
| Citrobacter freundii | S118A | (3) | − | 0.06 |
| Citrobacter freundii | S103B | (3) | − | ND |
| Citrobacter freundii | S135 | (3) | − | 0.06 |
| Citrobacter freundii | 621-64 | (18) | − | ND |
| Citrobacter freundii | 460-01 | (18) | − | ND |
| Citrobacter freundii | ATCC29935 | (2) | − | ND |
| Citrobacter freundii | ATCC33128 | (2) | − | ND |
| Citrobacter freundii | ATCC8090 | (2) | − | ND |
| Citrobacter freundii | Fanning 1 | (18) | − | ND |
| Citrobacter freundii | Fanning 2 | (18) | − | ND |
| Citrobacter freundii | Fanning 3 | (18) | − | ND |
| Citrobacter freundii | Fanning 4 | (18) | − | ND |
| Citrobacter freundii | Fanning 5 | (18) | − | ND |
| Citrobacter freundii | Fanning 5 | (18) | − | ND |
| Citrobacter freundii | 3104-61 | (19) | ND | 0.05 |
| Citrobacter freundii | 1636-61 | (19) | ND | 0.06 |
| Citrobacter freundii | 2990-58 | (19) | ND | 0.06 |
| Citrobacter freundii | 3062-62 | (19) | ND | 0.05 |
| Citrobacter freundii | 1637-71 | (19) | ND | 0.07 |
| Citrobacter freundii | 6440-59 | (19) | ND | 0.07 |
| Citrobacter freundii | 2970-59 | (19) | ND | 0.04 |
| Citrobacter freundii | 892-61 | (19) | ND | 0.09 |
| Citrobacter freundii | 3158-63 | (19) | ND | 0.06 |
| Enterobacter aerogenes | S123A | (3) | − | ND |
| Enterobacter aerogenes | ATCC29940 | (2) | − | ND |

TABLE 3-continued
E. COLI & SHIGELLA - EXCLUSIVITY DATA

| | | | | |
|---|---|---|---|---|
| *Enterobacter aerogenes* | ATCC13048 | (2) | — | 0.07 |
| *Enterobacter agglomerans* | S121B | (3) | — | 0.09 |
| *Enterobacter agglomerans* | PB | (1) | — | 0.04 |
| *Enterobacter agglomerans* | ATCC29917 | (2) | — | ND |
| *Enterobacter agglomerans* | ATCC29918 | (2) | — | ND |
| *Enterobacter agglomerans* | ATCC29919 | (2) | — | ND |
| *Enterobacter agglomerans* | ATCC29920 | (2) | — | ND |
| *Enterobacter agglomerans* | ATCC29921 | (2) | — | ND |
| *Enterobacter agglomerans* | ATCC29922 | (2) | — | ND |
| *Enterobacter agglomerans* | ATCC29923 | (2) | — | ND |
| *Enterobacter agglomerans* | ATCC29904 | (2) | — | ND |
| *Enterobacter agglomerans* | ATCC29915 | (2) | — | ND |
| *Enterobacter agglomerans* | ATCC29916 | (2) | — | ND |
| *Enterobacter agglomerans* | ATCC27998 | (2) | — | ND |
| *Enterobacter amnigenus* | ATCC33072 | (2) | — | ND |
| *Enterobacter cloacae* | S134 | (3) | — | 0.09 |
| *Enterobacter cloacae* | S121A | (3) | — | ND |
| *Enterobacter cloacae* | S121F | (3) | — | 0.06 |
| *Enterobacter cloacae* | 57 | (1) | — | ND |
| *Enterobacter cloacae* | 124 (lt. pnk) | (1) | — | ND |
| *Enterobacter cloacae* | 126 (lac+) | (1) | — | ND |
| *Enterobacter cloacae* | ATCC29941 | (2) | — | ND |
| *Enterobacter cloacae* | ATCC13047 | (2) | — | ND |
| *Enterobacter cloacae* | soy | (1) | ND | 0.05 |
| *Enterobacter cloacae* | IG3068 | (1) | ND | 0.07 |
| *Enterobacter cloacae* | S103B | (3) | ND | 0.08 |
| *Enterobacter cloacae* | ID118 | (1) | ND | 0.05 |
| *Enterobacter cloacae* | ID124 | (1) | ND | 0.09 |
| *Enterobacter cloacae* | ID101 | (1) | ND | 0.05 |
| *Enterobacter cloacae* | ID116 | (1) | ND | 0.07 |
| *Enterobacter cloacae* | ID128 | (1) | ND | 0.05 |
| *Enterobacter cloacae* | ID106 | (1) | ND | 0.05 |
| *Enterobacter gergoviae* | ATCC33028 | (2) | — | ND |
| *Enterobacter intermedium* | ATCC33110 | (2) | — | ND |
| *Enterobacter sakazakii* | ATCC29544 | (2) | — | ND |
| *Enterobacter sakazakii* | 108 (wheat) | (1) | — | 0.06 |
| *Enterobacter sakazakii* | 108 (wheat) | (1) | — | 0.12 |
| Enterobacter spp. CDC19 | wheat | (1) | — | ND |
| *Enterobacter taylorae* | ATCC35317 | (2) | — | ND |
| *Enterobacter taylorae* | A-F3 | (1) | ND | 0.09 |
| *Hafnia alvei* | ATCC29927 | (2) | — | ND |
| *Hafnia alvei* | 132 (lac−) | (1) | — | ND |
| *Klebsiella oxytoca* | ATCC13182 | (2) | — | 0.11 |
| *Klebsiella oxytoca* | ID112 | (1) | ND | 0.15 |
| *Klebsiella oxytoca* | S121C | (3) | — | 0.06 |
| *Klebsiella oxytoca* | RF501B | (1) | — | ND |
| *Klebsiella ozaenae* | ATCC11296 | (2) | — | ND |
| *Klebsiella planticola* | ATCC33531 | (2) | — | ND |
| *Klebsiella pneumoniae* | 69 (lt. pnk) | (1) | — | ND |
| *Klebsiella pneumoniae* | 72 (mauve) | (1) | — | ND |
| *Klebsiella pneumoniae* | 101 (drk. pnk) | (1) | — | ND |
| *Klebsiella pneumoniae* | ATCC13883 | (2) | — | ND |
| *Klebsiella pneumoniae* | ATCC29939 | (2) | — | ND |
| *Klebsiella terrigena* | ATCC33257 | (2) | — | ND |
| *Klebsiella pneumoniae* | S122F | (3) | ND | 0.05 |
| *Klebsiella pneumoniae* | IG3058 | (2) | ND | 0.06 |
| *Klebsiella pneumoniae* | ID117 | (2) | ND | 0.12 |
| *Klebsiella pneumoniae* | soy | (2) | ND | 0.10 |
| *Listeria innocua* | IG3171 | (1) | ND | 0.08 |
| *Listeria monocytogenes* | IG3168 | (1) | ND | 0.03 |
| *Listeria monocytogenes* | IG3157 | (1) | ND | 0.10 |
| *Listeria seeligeri* | IG3352 | (1) | ND | 0.05 |
| *Listeria seeligeri* | IG3381 | (1) | ND | 0.09 |
| *Listeria welshemeri* | IG3298 | (1) | ND | 0.10 |
| *Listeria welshemeri* | IG3289 | (1) | ND | 0.04 |
| Micrococcus spp. | IDisolate | (1) | ND | 0.07 |
| *Morganella morganii* | 47-24 (lac−) | (1) | — | ND |
| *Morganella morganii* | 134 (lac−) | (1) | — | ND |
| *Morganella morganii* | ATCC25830 | (2) | ND | 0.16 |
| *Pasturella gallinarum* | ATCC13361 | (2) | ND | 0.04 |
| *Pasturella multocida* | RF955 | (1) | — | ND |
| *Pasturella multocida* | ATCC19427 | (2) | ND | 0.08 |
| *Proteus mirabilis* | 134 (black) | (1) | — | ND |
| *Proteus mirabilis* | 117 (lac−) | (1) | — | ND |
| *Proteus mirabilis* | ATCC25933 | (2) | — | ND |
| *Proteus mirabilis* | ATCC29906 | (2) | — | ND |
| *Proteus mirabilis* | ATCC7002 | (2) | — | ND |
| *Proteus mirabilis* | IG3098 | (1) | ND | 0.07 |
| *Proteus mirabilis* | IG3109 | (1) | ND | 0.07 |
| *Proteus myxofaciens* | ATCC19692 | (2) | ND | 0.11 |
| *Proteus penneri* | ATCC33519 | (2) | ND | 0.09 |

TABLE 3-continued
E. COLI & SHIGELLA - EXCLUSIVITY DATA

| | | | | |
|---|---|---|---|---|
| Proteus vulgaris | ATCC13315 | (2) | ND | 0.12 |
| Proteus vulgaris | S118B | (3) | − | ND |
| Proteus vulgaris | S113 | (3) | − | ND |
| Providencia alcalifaciens | ATCC9886 | (2) | ND | 0.06 |
| Providencia alcalifaciens | ATCC27970 | (2) | ND | 0.06 |
| Providencia rettgeri | ATCC29944 | (2) | ND | 0.05 |
| Providencia rustigianii | ATCC33673 | (2) | ND | 0.05 |
| Providencia stuartii | ATCC29914 | (2) | ND | 0.06 |
| Pseudomonas acidovorans | ATCC15658 | (2) | ND | 0.07 |
| Pseudomonas aeruginosa | IG928 | (1) | ND | 0.13 |
| Pseudomonas pickettii | QCisolate | (1) | ND | 0.11 |
| Pseudomonas spp. | S107 | (3) | − | ND |
| Salmonella arizonae | RF914 | (1) | ND | 0.10 |
| Salmonella arizonae | S942 | (3) | ND | 0.20 |
| Salmonella typhimurium | ATCC23566 | (2) | − | 0.07 |
| Salmonella weslaco | RF851 | (1) | ND | 0.13 |
| Staphylococcus aureus | ATCC12600 | (2) | ND | 0.09 |
| Staphylococcus aureus | IDisolate | (1) | ND | 0.06 |
| Staphylococcus epidermidis | ATCC14990 | (2) | ND | 0.06 |
| Staphylococcus epidermidis | IDisolate | (1) | ND | 0.10 |
| Staphylococcus saprophyticus | ATCC15303 | (2) | ND | 0.08 |
| Streptococcus agalactiae | ATCC13813 | (2) | ND | 0.06 |
| Streptococcus faecalis | ATCC19433 | (2) | ND | 0.06 |
| Streptococcus faecium | ATCC6056 | (2) | ND | 0.06 |
| Streptococcus pneumoniae | ATCC6303 | (2) | ND | 0.06 |
| Streptococcus pyogenes | ATCC19615 | (2) | ND | 0.06 |
| Streptococcus salivarius | ATCC13419 | (2) | ND | 0.06 |
| Streptococcus sanguis | ATCC10556 | (2) | ND | 0.07 |
| Streptococcus mutans | ATCC25175 | (2) | ND | 0.06 |
| Serratia marcescens | ATCC29937 | (2) | − | ND |
| Serratia odorifera | 83 (mauve) | (1) | − | ND |
| Serratia spp. | 106 (lac−) | (1) | − | ND |
| Yersinia enterocolitica D255 | RF953 | (1) | − | ND |
| Yersinia enterocolitica 1625 | RF954 | (1) | − | ND |
| Yersinia enterocolitica | ATCC9610 | (2) | ND | 0.08 |
| Yersinia enterocolitica | ATCC23715 | (2) | ND | 0.12 |
| Yersinia enterocolitica | ATCC27729 | (2) | ND | 0.03 |
| Yersinia frederiksenii | ATCC33641 | (2) | ND | 0.07 |
| Yersinia intermedia | ATCC29909 | (2) | ND | 0.05 |
| Yersinia kristensenii | ATCC29911 | (2) | ND | 0.12 |
| Yersinia kristensenii | ATCC33638 | (2) | ND | 0.06 |
| Yersinia philomiragia | ATCC25015 | (2) | ND | 0.07 |
| Yersinia pseudotuberculosis | ATCC29833 | (2) | ND | 0.08 |
| Yersinia pseudotuberculosis | ATCC29910 | (2) | ND | 0.16 |
| Yersinia ruckeri | ATCC29473 | (2) | ND | 0.21 |
| Yersinia ruckeri | ATCC29908 | (2) | ND | 0.15 |

Key for Dot Blot Hybridization Index
++++ = positive control level of hybridization
+++ = strong hybridization
++ = weak but readily detectable
+ = barely detectable
− = zero
ND = not determined
Source key:
(1) GENE-TRAK Systems, Framingham, MA.
(2) American Type Culture Collection, Bethesda, MD.
(3) Silliker Laboratories, Chicago, Illinois
(4) Grace Thorne, The Children's Hospital, Boston
(5) Steven Moseley, Seattle Children's Hospital
(6) K. Wachsmuth, CED, Atlanta
(7) Richard Hull, Baylor college of Medicine, Houston TX.
(8) Massachusetts General Hospital
(9) Gary Doern, Universitiy of Mass. Medical Center
(10) Don Goldmann, Boston Children's Hospital
(11) Susan Gibson, Texas Health Department
(12) Madigan Army Medical Center
(13) Samuel Formal, Walter Reed Army Institute of Research
(14) Ellen Crotty, University Hospital, Cleveland
(15) Thomas Gavan, Cleveland Clinic Foundation
(16) C. W. Shuster, Case Western Reserve University
(17) Deibel Laboratory, Madison, WI
(18) George Fanning, Walter Reed Army Hospital, Washington, D.C.
(19) Don Brenner, CDC, Atlanta, GA.

TABLE 4
EXAMPLE 1 - SPECIFIC

| | Cells/ | Hybridization[a] Results | Microbiological[b] Confirmation |
|---|---|---|---|

TABLE 4-continued

| # | Sample | Source | Species | Strain | Sample | $A_{450}$ | GT | L-EMB | GAS |
|---|---|---|---|---|---|---|---|---|---|
| 1 | Non-fat Dry Milk | (1) | E. coli | 3116 | 700 | 2.14 | 1 | 1 pos | 1 pos |
| 2 | Non-fat Dry Milk | (1) | E. coli | 140 | 140 | 2.12 | 1 | 1 | 1 |
| 3 | Non-fat Dry Milk | | control | | | 0.09 | 0 | ND | 0 neg |
| 4 | Coconut | (1) | E. coli | 3124 | 370 | 2.26 | 1 | 1 | 1 |
| 5 | Coconut | (1) | E. coli | 3124 | 74 | 2.13 | 1 | 1 | 1 |
| 6 | Coconut | | control | | | 0.09 | 0 | ND | 0 |
| 7 | Pecans | (2) | E. coli | 077 | 330 | 2.20 | 1 | 1 | 1 |
| 8 | Pecans | (2) | E. coli | 077 | 60 | 2.24 | 1 | 1 | 1 |
| 9 | Pecans | | control | | | 0.12 | 0 | ND | 0 |
| 10 | Beef franks | (1) | E. coli | 3140 | 580 | 2.20 | 1 | 1 | 1 |
| 11 | Beef franks | (1) | E. coli | 3140 | 118 | 2.18 | 1 | 1 | 1 |
| 12 | Beef franks | | control | | | 0.08 | 0 | ND | 0 |
| 13 | Pudding | (1) | E. coli | 3125 | 525 | 2.21 | 1 | 1 | 1 |
| 14 | Pudding | (1) | E. coli | 3125 | 105 | 2.16 | 1 | 1 | 1 |
| 15 | Pudding | | control | | | 2.11 | 0 | ND | 0 |
| 16 | Frozen fish | (2) | E. coli | 074 | 385 | 2.11 | 1 | 1 | 1 |
| 17 | Frozen fish | (2) | E. coli | 074 | 77 | 2.19 | 1 | 1 | 1 |
| 18 | Frozen fish | | control | | | 0.13 | 0 | ND | 0 |
| 19 | Egg Beaters | (1) | E. coli | 3117 | 890 | 2.20 | 1 | 1 | 1 |
| 20 | Egg Beaters | (1) | E. coli | 3117 | 176 | 2.18 | 1 | 1 | 1 |
| 21 | Egg Beaters | | control | | | 0.09 | 0 | ND | 0 |
| 22 | Cheddar | (1) | E. coli | 3136 | 910 | 2.20 | 1 | 1 | 1 |
| 23 | Cheddar | (1) | E. coli | 3136 | 183 | 2.18 | 1 | 1 | 1 |
| 24 | Cheddar | | control | | | 0.07 | 0 | ND | 0 |
| 25 | Cottage cheese | (1) | E. coli | 3124 | 370 | 2.16 | 1 | 1 | 1 |
| 26 | Cottage cheese | (1) | E. coli | 3124 | 74 | 1.87 | 1 | 1 | 1 |
| 27 | Cottage cheese | | control | | | 0.09 | 0 | ND | 0 |
| 28 | Chocolate | (2) | E. coli | 075 | 695 | 2.03 | 1 | 1 | 1 |
| 29 | Chocolate | (2) | E. coli | 075 | 139 | 1.96 | 1 | 1 | 1 |
| 30 | Chocolate | | control | | | 0.10 | 0 | ND | 0 |

RESULTS OF NON-ISOTOPIC, IN-HOUSE E. COLI FOOD TRIAL NUMBER 9
[a]Non-isotopic hybridization results, procedure described in Example 1 - Specific
$A_{450}$ = Absorbance at 450 nm
GT pos(itive) = Abs. >0.25
GT neg(ative) = Abs. <0.25
control = no strain inoculated
ND = not done
[b]Nicrobiological confirmation results
L-EMB pos(itive) = growth on EMB agar plates producing typical colonies followed by biochemical confirmation
L-EMB neg(ative) = no typical E. coli
Gas = gas production (pos.) or no gas product (neg) in lactose containing broth
Source key:
(1) Grace Thorne, The Children's Hospital, Boston
(2) Silliker Laboratories, Chicago Heights, Illinois SUMMARY OF RESULTS
Microbiological Confirmation (L-EMB)

| | | + | − |
|---|---|---|---|
| Non-isotopic | + | 20 | 0 |
| Hybridization | − | 0 | 10 |

What is claimed is:

1. A nucleic acid fragment capable of hybridizing, under predetermined stringency conditions, to rRNA or rDNA (rRNA gene) of E. coli Shigella and not to rRNA or DNA of non-E. coli/Shigella.

2. The nucleic acid fragment of claim 1 wherein said fragment is capable of hybridizing to at least 95% of E. coli and Shigella strains.

3. The nucleic acid fragment of claim 1, said fragment being capable of hybridizing under hybridizing conditions to nucleic acid to which probe 787 is capable of hybridizing.

4. The nucleic acid fragment of claim 1 wherein said fragment is homologous with at least 95% of a sequence comprising at least any ten consecutive nucleotides within region 455 to 477 of the 16S rRNA of E. coli.

5. A method for detecting the presence of E. coli and/or Shigella in a sample comprising:
 a) contacting the nucleic acid fragment of claim 1 with said sample under conditions that allow said fragment to hybridize to rRNA of E. coli and/or Shigella, if present in said sample, and
 b) detecting said hybrid complexes as an indication of the presence of said E. coli and/or Shigella in said sample.

6. The method of claim 5 wherein said nucleic acid fragment is capable of hybridizing under hybridizing conditions to nucleic acid to which probe 787 is capable of hybridizing.

7. An assay kit for detecting E. coli and/or Shigella comprising the nucleic acid fragment of claim 1 packaged in at least one container, and instructions for utilizing said nucleic acid fragment for detecting E. coli and/or Shigella.

8. An assay kit for detecting E. coli and/or Shigella comprising the nucleic acid fragment of capable of hybridizing under hybridizing conditions to probe 787 packaged in at least one container, and instructions for utilizing said nucleic acid fragment for detecting E. coli and/or Shigella.

9. A nucleic acid fragment capable of hybridizing under predetermined stringency conditions to rRNA or rDNA (rRNA gene) of E. coli and Shigella and not to rRNA or DNA of non-E. coli/Shigella wherein said fragment is homologous with at least 95l% of a sequence comprising at least any ten consecutive nucleotides within a region of 455 to 477 of the 16S rRNA of *E. coli*.

10. The nucleic acid fragment of claim 1 wherein said fragment is not capable of hybridizing appreciably, under said conditions, to r RNA or DNA of *Aeromonas sobria, Bacillus cereus, Candida albicans, Citrobacter freundii, Escherichia vulneris, Enterobacter agglomerans,* *Enterobacter cloacae, Klebsiella pneumoniae, Klebsiella oxytoca, Listeria monocytogenes, Pseudomonas aeruginosa, Salmonella arizonae, Serratia odorifera, Staphylococcus aureus, Staphylococcus epidermidis, Staphylococcus saprohyricus, Streptococcus agalactiae, Streptococcus faecalis, Streptococcus faecium, Streptococcus mutants, Streptococcus pneumoniae.*

* * * * *